United States Patent [19]

Hauck et al.

[11] 4,103,094
[45] Jul. 25, 1978

[54] CYCLOHEXANETETROL ALKANOATES

[75] Inventors: Frederic P. Hauck, Somerville; Rita T. Fox, Princeton, both of N.J.

[73] Assignee: E. R. Squibb & Sons, Inc., Princeton, N.J.

[21] Appl. No.: 795,465

[22] Filed: May 10, 1977

[51] Int. Cl.$^2$ ............................................. C07D 69/12
[52] U.S. Cl. .................................. 560/231; 544/394; 544/399; 260/295 R; 424/250; 424/263; 424/267; 260/348.62
[58] Field of Search .................... 260/208 R, 268 PH; 560/231

[56] References Cited

U.S. PATENT DOCUMENTS 3,936,465   2/1976   Hauck et al. ..................... 260/293.65

OTHER PUBLICATIONS

Burger, Medicinal Chemistry 2nd Edition, Interscience Publishers, Inc. New York, (1960).

*Primary Examiner*—Jose Tovar
*Attorney, Agent, or Firm*—Lawrence S. Levinson; Merle J. Smith; Donald J. Barrack

[57] ABSTRACT

Compounds having the formula

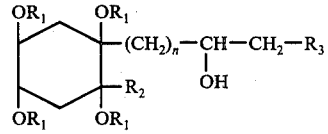

and the pharmaceutically acceptable salts thereof, wherein $R_1$ is alkanoyl; $R_2$ is alkyl; $R_3$ is alkylamino, dialkylamino, a 1-piperazinyl group, 4-aryl-1,2,3,6-tetrahydro-1-pyridinyl, or N-alkyl-N-(pyridinylalkyl)amino; and $n$ is 1, 2, or 3; have useful hypotensive activity.

2 Claims, No Drawings

CYCLOHEXANETETROL ALKANOATES

BACKGROUND OF THE INVENTION

U.S. Pat. No. 3,936,465, issued Feb. 3, 1976, encompasses within its disclosure compounds having the formula

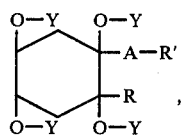

wherein Y is alkanoyl, R is hydrogen or alkyl, R' is alkylamino or dialkylamino and A is alkylene. The compounds are disclosed as useful for the treatment of hypertension.

Aminoalkanol derivatives of a varied nature have been investigated in the field of medicinal chemistry. A review of some of these compounds, and of their various utilities is included in Burger, *Medicinal Chemistry*, second edition, Interscience Publishers, Inc., New York, 1960. Various aminoalkanol derivatives having the general formula

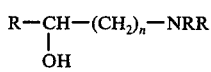

are described as having cholinergic, pressor, central nervous system stimulant, vasoconstrictor and antimalarial activity.

The Burger test, supra., also discusses the hypotensive activity of veratrum alkaloids. The hypotensive activity of crude plant extracts containing veratrum alkaloids is largely attributable to ester alkaloids.

BRIEF DESCRIPTION OF THE INVENTION

Compounds having the formula

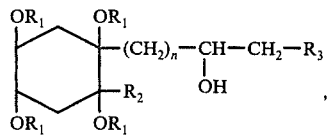

and the pharmaceutically acceptable salts thereof, have cardiovascular activity. In formula I, and throughout the specification, the symbols are as defined below.

$R_1$ is alkanoyl having 1 to 7 carbon atoms; acetyl is the preferred alkanoyl group.

$R_2$ is alkyl; methyl is preferred;

$R_3$ is alkylamino, dialkylamino, 1-piperazinyl, 4-alkyl-1-piperazinyl, 4-aryl-1-piperazinyl, 4-aryl-1,2,3,6-tetrahydro-1-pyridinyl, N-alkyl-N-[(2-pyridinyl)alkyl]amino, N-alkyl-N-[(3-pyridinyl)alkyl]amino or N-alkyl-N-[(4-pyridinyl)alkyl]amino; and n is 1, 2 or 3.

The term "aryl", as used throughout the specification, refers to phenyl or phenyl substituted with one or two halogen (fluorine, chlorine, bromine, or iodine), alkyl, trifluoromethyl, alkoxy or alkylthio groups.

The terms "alkyl", "alkoxy", and "alkylthio", as used throughout the specification, refer to groups having 1 to 6 carbon atoms.

DETAILED DESCRIPTION OF THE INVENTION

The compounds of this can be prepared by reacting an oxirane compound having the formula

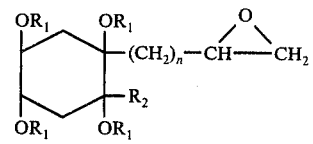

with a nitrogen containing compound having the formula $$R_3\text{—H.} \qquad \qquad \text{III}$$

Reaction conditions are not critical, but the reaction proceeds more rapidly when carried out with heating in an organic solvent, or mixture of organic solvents, e.g., benzene, glacial acetic acid, ethanol, etc.

The oxirane compounds of formula II are readily obtained from a corresponding cyclohexanetetrol derivative having the formula

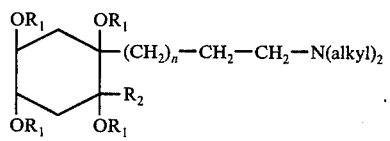

Compounds of formula IV are known; see, for example, U.S. Pat. No. 3,936,465 issued Feb. 3, 1976. Oxidation of a compound of formula IV yields the corresponding N-oxide having the formula

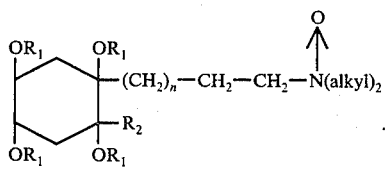

Exemplary of the oxidizing agents which may be used are the peracids, e.g., m-chloroperbenzoic acid.

Vacuum pyrolysis of an N-oxide of formula V yields an olefin having the formula

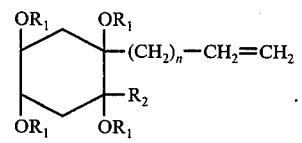

Oxidation of an olefin of formula VI yields the corresponding oxirane compound of formula II. Exemplary of the oxidizing agents which may be used are the peracids, e.g., m-chloroperbenzoic acid.

The oxirane compounds of formula II and the olefins of formula VI are novel intermediates which are useful in the preparation of the compounds of formula I, and as such, constitute an integral part of this invention.

The compounds of formula I can be converted to their pharmaceutically acceptable acid-addition salts with both organic and inorganic acids using methods well known in the art. Exemplary salts are hydrohalides (e.g., hydrochloride and hydrobromide), nitrate, phosphate, borate, acetate, tartrate, methanesulfonate, benzenesulfonate, toluenesulfonate and the like.

Formula I includes all stereoisomers and mixtures thereof. Particular stereoisomers are prepared by utilizing as the starting material the compound of formula IV with the corresponding stereoisomerism. The preferred stereoisomers are those in which the $OR_1$ groups are all axial.

The compounds of formula I, and the pharmaceutically acceptable salts thereof, are useful as hypotensive agents in mammals, e.g., domestic animals such as dogs and cats. Daily doses of from 5 to 50 milligrams per kilogram of animal body weight, preferably about 5 to 25 milligrams per kilogram of animal body weight, can be administered in single or divided doses. Both oral and parenteral administration are specifically contemplated.

EXAMPLE 1

1,2:1,4:4,5-trans-1-[4-(Dimethylamino)-3-hydroxybutyl]-2-methyl-1,2,4,5-cyclohexanetetrol, 1,2,4,5-tetraacetate ester

A.

1,2:1,4:4,5-trans-1-[4-(Dimethylamino)butyl]-2-methyl-1,2,4,5-cyclohexanetetrol, tetraacetate ester, N-oxide A solution of 8.5 g of 1,2:1,4:4,5-trans-1-[4-(dimethylamino)butyl]-2-methyl-1,2,4,5-cyclohexanetetrol, tetraacetate ester in 200 ml of chloroform is cooled in an ice bath and 4.4 g of 85% m-chloroperbenzoic acid is added. The mixture is warmed to room temperature over 5 hours. The solution is partially evaporated in vacuo to one-third its volume and chromatographed on 400 g of neutral Alumina III (wet-packed in chloroform). The column is eluted with 600 ml of chloroform to remove any forerun and then the N-oxide product is eluted with 650 ml of 20% methanolic chloroform to give 10.4 g of oil Crystallization from ethyl acetate give 7.45 g of a hydroscopic white solid, melting point 128°–130° C.

B.

1,2:4:4,5-trans-1-Methyl-2-(3-butenyl)-1,2,4,5-cyclohexanetetrol, tetraacetate ester An amount of 6.4 g of the above N-oxide is heated in a vacuum distillation set-up under 30 mm Hg vacuum with nitrogen bleed until all the solid is melted and vigorous evolution of volatile side products cease. The vacuum is then improved to 2–3 mm Hg and the product distilled as a pale yellow liquid which crystallizes on standing to give 4.55 g of the olefin as a white solid; boiling point of distillate 180°–200°0 C (mainly 195° C), at 2–3 mm Hg.

C.

1,2:1,4:4,5-trans-1-Methyl-2-(2-oxiranylethyl)-1,2,4,5-cyclohexanetetrol, tetraacetate ester A solution of 2.0 g of the above tetraacetate-olefin and 1.05 g of 85% m-chloroperbenzoic acid in 50 ml of chloroform is prepared at 0° C and stirred for about 16 hours at room temperature. The solution is then suction filtered through 30 g of neutral Alumina III. The alumina is washed with 100 ml of chloroform and the combined filtrate evaporated in vacuo to give a colorless oil, which solidifies on standing to give 1.85 g of the epoxide product as a white solid.

D.

1,2:1,4:4,5-trans-1-[4-(Dimethylamino)-3-hydroxybutyl]-2-methyl-1,2,4,5-cyclohexanetetrol, 1,2,4,5-tetraacetate ester An amount of 20 ml of 3.87 M dimethylamine in benzene is added to a solution of 2.0 g of the tetraacetate-epoxide in 80 ml of benzene in a Parr bomb. The bomb is heated for about 16 hours at 100°±5° C. The bomb is cooled to room temperature and the solution evaporated in vacuo to give 2.3 g of oil. An acid-base extraction gives 1.65 g of basic material. Crystallization from 10 ml of 1:1 ethyl acetatehexane yields 564 mg of the title compound, melting point 94°–105° C.

Anal. Calc'd. for $C_{21}H_{45}NO_9$ (445.5 g/m): C, 56.61; H, 7.92; N, 3.14. Found: C, 56.50; H, 7.86; N, 3.21.

EXAMPLE 2

1,2:1,4:4,5-trans-1-[3-Hydroxy-4-[4-(2-methoxyphenyl)-1-piperazinyl]butyl]-2-methyl-1,2,4,5-cyclohexanetetrol, 1,2,4,5-tetraacetate ester, hydrochloride (1:1)

A solution of 1.4 g of 1-(2-methoxyphenyl)piperazine and 3.0 g of 1,2:1,4:4,5-trans-1-methyl-2-(oxiranylethyl)-1,2,4,5-cyclohexanetetrol, tetraacetate ester in 50 ml of absolute ethanol and 20 ml of benzene is stirred for about 16 hours at 55° C. The solvent is removed in vacuo, and the 4.5 g of residue is dissolved in ether and treated with an anhydrous solution of hydrogen chloride in isopropanol to yield a solid. The solid is collected, washed with ether and dried in vacuo. [The ether solution is washed (dilute hydrochloric acid, water and a saturated solution of sodium chloride), dried and evaporated in vacuo to give 0.55 g of recovered epoxide starting material.] The hydrochloride salt does not recrystallize. It is dissolved in water, made alkaline with cold concentrated ammonium hydroxide and extracted with chloroform to give 3.5 g of an oil-foam mixture. Crystallization from ether gives 2.6 g of the free base as a solid. Conversion of the free base to the monohydrochloride salt, and recrystallization for ethyl acetatemethanol gives 2.0 g of the title compound as a crystalline solid, melting point 213°–217° C.

Anal. Calc'd. for $C_{30}H_{40}N_2O_{10}$·HCl: C, 57.27; H, 7.21; N, 4.45; Cl, 5.64. Found: C, 57.26; H, 7.50; N, 4.32; Cl, 5.66

EXAMPLE 3

1,2:1,4:4,5-trans-1-[3-Hydroxy-4-[methyl[2-(2-pyridinyl)ethyl]-amino]butyl]-2-methyl-1,2,4,5-cyclohexanetetrol, tetraacetate ester, hydrochloride (1:2)

A solution of 1.7 g of 1,2:1,4:4,5-trans-1-methyl-2-(oxiranylethyl)-1,2,4,5-cyclohexanetetrol, tetraacetate ester (prepared as described in Example 1C) and 0.58 g of 2-(β-methylaminoethyl)pyridine in benzene and absolute ethanol (15:37.5) is stirred at 57° C for about 16 hours. The solvent is removed in vacuo and the 2.25 g of residue is chromatographed on 100 g of neutral Alumina III. Elution with 800 ml of 25–45% ethyl acetatehexane gives 0.4 g of forerun (mainly epoxide). Elution with 800 ml of 50–60% ethyl acetate-hexane and 600 ml of 5% methanol-ethyl acetate gives 1.1 g of the desired product as an oil. This material is dissolved in ether and converted to the dihydrochloride salt. Two recrystallizations from methanol-ethyl acetate give 0.82 g of the title compound, melting point 186°–187.5° C.

*Anal. Calc'd.* for $C_{27}H_{40}N_2O_9 \cdot HCl$ (573.1/609.6 g/m): C, 53.20; H, 6.95; N, 4.60; Cl, 11.63. Found: C, 53.07; H, 7.05; N, 4.53; Cl, 11.55.

EXAMPLE 4

1,2:1,4:4,5-trans-1-[3-Hydroxy-4-(3,6-dihydro-4-phenyl-1(2H)-pyridinyl)butyl]-2-methyl-1,2,4,5-cyclohexanetetrol, tetraacetate ester A solution of 1.65 g of 1,2:1,4:4,5-trans-1-methyl-2-(2-oxiranylethyl)-1,2,4,5-cyclohexanetetrol, tetraacetate esters (prepared as described in Example 1C) and 0.69 g of 4-phenyl-1,2,3,6-tetrahydropyridine in benzene-absolute ethanol (15:37.5) is stirred at 57° C for about 16 hours. The solution is evaporated in vacuo and the residue crystallized from ether-hexane to give 1.1 g of solid. An additional 0.6 g is obtained from the next two crops. The 1.7 g of combined solid is recrystallized from ethyl acetate-hexane to give 0.80 g of the title compound, melting point 142°–147° C.

*Anal. Calc'd.* for $C_{30}H_{41}NO_9$ (559.67 g/m): C, 64.38; H, 7.38; N, 2.50. Found: C, 64.33; H, 7.47; N, 2.43.

EXAMPLES 5–18

Following the procedure of Example 1, but substituting the compound listed in column I for dimethylamine, yields the compound listed in column II.

|    | Column I | Column II |
|----|----------|-----------|
| 5  | methylamine | 1,2:1,4:4,5-trans-1-[4-(methylamino)-3-hydroxybutyl]-2-methyl-1,2,4,5-cyclohexanetetrol, 1,2,4,5-tetraacetate ester |
| 6  | 1-piperazine | 1,2:1,4:4,5-trans-1-[3-hydroxy-4-(1-piperazinyl)butyl]-2-methyl-1,2,4,5-cyclohexanetetrol, 1,2,4,5-tetraacetate ester |
| 7  | 1-methylpiperazine | 1,2:1,4:4,5-trans-1-[3-hydroxy-4-(4-methyl-1-piperazinyl)butyl]-2-2 methyl-1,2,4,5-cyclohexanetetrol, 1,2,4,5-tetraacetate ester |
| 8  | 1-phenylpiperazine | 1,2:1,4:4,5-trans-1-[3-hydroxy-4-(4-phenyl-1-piperazinyl)butyl]-2-methyl-1,2,4,5-cyclohexanetetrol, 1,2,4,5-tetraacetate ester |
| 9  | 1-(2-methylphenyl)-piperazine | 1,2:1,4:4,5-trans-1-[3-hydroxy-4-[4-(2-methylphenyl)-1-piperazinyl]-butyl]-2-methyl-1,2,4,5-cyclohexanetetrol, 1,2,4,5-tetraacetate ester |
| 10 | 1-[3-(trifluoromethyl)-phenyl]piperazine | 1,2:1,4:4,5-trans-1-[3-hydroxy-4-[4-[3-(trifluoromethyl)phenyl]-1-piperazinyl]butyl]-2-methyl-1,2,4,5-cyclohexanetetrol, 1,2,4,5-tetraacetate ester |
| 11 | 1-[2-(methylthio)phenyl]-piperazine | 1,2:1,4:4,5-trans-1-[3-hydroxy-4-[4[2-(methylthio)phenyl]-1-piperazinyl]butyl]-2-methyl-1,2,4,5-cyclohexanetetrol, 1,2,4,5-tetraacetate ester |
| 12 | 1-(4-chlorophenyl)-piperazine | 1,2:1,4:4,5-trans-1-[4-(4-chlorophenyl)-1-piperazinyl]-3-hydroxybutyl]-2-methyl-1,2,4,5-cyclohexanetetrol, 1,2,4,5-tetraacetate ester |
| 13 | 3-(β-methylaminoethyl)-pyridine | 1,2:1,4:4,5-trans-1-[3-hydroxy-4-[methyl[2-(3-pyridinyl)ethyl]ethyl]amino]-butyl]-2-methyl-1,2,4,5-cyclohexanetetrol, tetraacetate ester |
| 14 | 4-(γ-methylaminopropyl)-pyridine | 1,2:1,4:4,5-trans-1-[3-hydroxy-4-[methyl[3-(4-pyridinyl)propyl]-amino]butyl]-2-methyl-1,2,4,5-cyclohexanetetrol, tetraacetate ester |
| 15 | 4-(2-ethylphenyl)-1,2,3,6-tetrahydro-pyridine | 1,2:1,4:4,5-trans-1-[3-hydroxy-4-[3,6-dihydro-4-[(2-ethylphenyl)-1(2H)-pyridinyl]butyl]-2-methyl-1,2,4,5-cyclohexanetetrol, tetraacetate ester |
| 16 | 4-(2-ethylthiophenyl)-1,2,3,6-tetrahydro-pyridine | 1,2:1,4:4,5-trans-1-[3-hydroxy-4-[3,6-dihydro-4-[(2-ethylthiophenyl)-1(2H)-pyridinyl]butyl]-2-methyl-1,2,4,5-cyclohexanetetrol, tetraacetate ester |
| 17 | 4-(3-trifluoromethylphenyl)-1,2,3,6-tetra-hydropyridine | 1,2:1,4:4,5-trans-1-[3-hydroxy-4-[3,6-dihydro-4-[(3-trifluoromethylphenyl)-1(2H)-pyridinyl]butyl]-2-methyl-1,2,4,5-cyclohexanetetrol, tetraacetate ester |
| 18 | 4-(4-bromophenyl)-1,2,-3,6-tetrahydropyridine | 1,2:1,4:4,5-trans-1-[3-hydroxy-4-[(3,6-dihydro-4-[(4-bromophenyl)-1(2H)-pyridinyl]butyl]-2-methyl-1,2,4,5-cyclohexanetetrol, tetraacetate ester |

EXAMPLES 19–20

Following the procedure of Example 1, but substituting the compound listed in column I for 1,2:1,4:4,5-trans-1-[4-(dimethylamino)butyl]-2-methyl-1,2,4,5-cyclohexanetetrol, tetraacetate ester, yields the compound listed in column II.

|    | Column I | Column II |
|----|----------|-----------|
| 19 | 1,2:1,4:4,5-trans-1-[3-(dimethylamino)propyl]-2-methyl-1,2,4,5-cyclohexanetetrol, tetraacetate ester | 1,2:1,4:4,5-trans-1-[3-(dimethylamino)-2-hydroxypropyl]-2-methyl-1,2,4,5-cyclohexanetetrol, 1,2,4,5-tetraacetate ester |
| 20 | 1,2:1,4:4,5-trans-1-[5-(dimethylamino)pentyl]-2-methyl-1,2,4,5-cyclohexanetetrol, tetraacetate ester | 1,2:1,4:4,5-trans-1-[5-(dimethylamino)-4-hydroxypentyl]-2-methyl-1,2,4,5-cyclohexanetetrol, 1,2,4,5-tetraacetate ester |

What is claimed is:

1. A compound having the formula

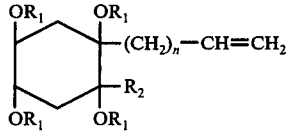

wherein $R_1$ is alkanoyl having 1 to 7 carbon atoms; $R_2$ is alkyl having 1 to 6 carbon atoms; and $n$ is 1, 2 or 3.

2. The compound in accordance with claim 1, 1,2:1,4:4,5-trans-1-methyl-2-(3-butenyl)-1,2,4,5-cyclohexanetetrol, tetraacetate ester.

* * * * *

UNITED STATES PATENT AND TRADEMARK OFFICE
CERTIFICATE OF CORRECTION

PATENT NO. : 4,103,094
DATED : July 25, 1978
INVENTOR(S) : Frederic P. Hauck et al It is certified that error appears in the above-identified patent and that said Letters Patent are hereby corrected as shown below:

Column 3, line 44 "1,2:4:4,5" should read --1,2:1,4:4,5--.

Column 3, line 54 "200°0C" should read --200°C--.

Example 11, column II line 2 "[4[2" should read --[4-[2--.

Example 18, column II line 2 "[(3," should read --[3,--.

Signed and Sealed this

Ninth Day of January 1979

[SEAL]

Attest:

RUTH C. MASON
Attesting Officer

DONALD W. BANNER
Commissioner of Patents and Trademarks